United States Patent
McInnes et al.

(10) Patent No.: US 9,328,139 B2
(45) Date of Patent: May 3, 2016

(54) CYCLIN BASED INHIBITORS OF CDK2 AND CDK4

(71) Applicants: Campbell McInnes, Irmo, SC (US); Shu Liu, Belmont, CA (US)

(72) Inventors: Campbell McInnes, Irmo, SC (US); Shu Liu, Belmont, CA (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/017,988

(22) Filed: Sep. 4, 2013

(65) Prior Publication Data

US 2014/0316107 A1 Oct. 23, 2014

Related U.S. Application Data

(62) Division of application No. 13/088,694, filed on Apr. 18, 2011, now Pat. No. 8,566,072.

(60) Provisional application No. 61/342,598, filed on Apr. 16, 2010.

(51) Int. Cl.
| | |
|---|---|
| *A61K 38/04* | (2006.01) |
| *C07K 7/02* | (2006.01) |
| *G06F 19/16* | (2011.01) |
| *C07D 275/00* | (2006.01) |
| *C07D 277/00* | (2006.01) |
| *C07D 333/10* | (2006.01) |
| *C07K 7/06* | (2006.01) |
| *G06F 19/18* | (2011.01) |

(52) U.S. Cl.
CPC . *C07K 7/06* (2013.01); *G06F 19/16* (2013.01); *G01N 2500/02* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 7,449,544 B2 * | 11/2008 | Zheleva et al. | 530/317 |
| 2003/0129656 A1 | 7/2003 | Park et al. | |
| 2003/0171904 A1 | 9/2003 | Lewis et al. | |
| 2003/0187220 A1 | 10/2003 | Park et al. | |
| 2003/0225527 A1 | 12/2003 | Antonysamy et al. | |
| 2004/0229290 A1 | 11/2004 | Hellinga et al. | |

FOREIGN PATENT DOCUMENTS

WO  WO 2005042565  5/2005

OTHER PUBLICATIONS

Zheleva 2002, J. Peptide Res., 60, 257-270.*
Website:http://cancerweb.ncl.ac.uk/omd/about.html, retreived on Jul. 7, 2005.*
Website: http://www.onelook.com/?w=constituent&ls=a, retreived on Jun. 29, 2015.*
Andrews MJI, McInnes C, Kontopidis G, Innes L, Cowan A, Plater A, Fischer PM: Design, synthesis, biological activity and structural analysis of cyclic peptide inhibitors targeting the substrate recruitment site of cyclin-dependent kinase complexes. *Organic & Biomolecular Chemistry* 2004, 2:2735-2341.
Andrews MJ, Kontopidis G, McInnes C, Plater A, Innes L, Cowan A, Jewsbury P, Fischer PM: Replace: a strategy for iterative design of cyclin-binding groove inhibitors. *Chembiochem* 2006, 7:1909-1915.
Ball KL, Lain S, Fåhraeus R, Smythe C, Lane DP: Cell-cycle arrest and inhibition of Cdk4 activity by small peptides based on the carboxy-terminal domain of p21WAF1. *Current Biology* 1996, 7:71-80.
Baughn LB, Di Liberto M, Wu K, Toogood PL, Louie T, Gottschalk R, Niesvizky R, Cho H, Ely S, Moore MA, et al.: A novel orally active small molecule potently induces G1 arrest in primary myeloma cells and prevents tumor growth by specific inhibition of cyclin-dependent kinase 4/6. *Cancer Res* 2006, 66:7661-7667.
Blain SW: Switching cyclin D-Cdk4 kinase activity on and off. *Cell Cycle* 2008, 7:892-898.
Brown NR, Noble ME, Endicott JA, Johnson LN: The structural basis for specificity of substrate and recruitment peptides for cyclin-dependent kinases. *Nature Cell Biology* 1999, 1:438-443.
Chen YN, Sharma SK, Ramsey TM, Jiang L, Martin MS, Baker K, Adams PD, Bair KW, Kaelin WG, Jr.: Selective killing of transformed cells by cyclin/cyclin-dependent kinase 2 antagonists. *Proc Natl Acad Sci U S A* 1999, 96:4325-4329.
Kontopidis G, Andrews MJ, McInnes C, Plater A, Innes L, Renachowski S, Cowan A, Fischer PM: Truncation and optimisation of peptide inhibitors of cyclin-dependent kinase 2-cyclin a through structure-guided design. *ChemMedChem* 2009, 4:1120-1128.
Day PJ, Cleasby A, Tickle IJ, O'Reilly M, Coyle JE, Holding FP, McMenamin RL, Yon J, Chopra R, Lengauer C, et al.: Crystal structure of human CDK4 in complex with a D-type cyclin. *Proc Natl Acad Sci U S A* 2009, 106:4166-4170.
Fischer PM, Gianella-Borradori A: Recent progress in the discovery and development of cyclin-dependent kinase inhibitors. *Expert Opin Investig Drugs* 2005, 14:457-477.
Fry DW, Harvey PJ, Keller PR, Elliott WL, Meade M, Trachet E, Albassam M, Zheng X, Leopold WR, Pryer NK, et al.: Specific inhibition of cyclin-dependent kinase 4/6 by PD 0332991 and associated antitumor activity in human tumor xenografts. *Molecular Cancer Therapeutics* 2004, 3:1427-1438.
James MK, Ray A, Leznova D, Blain SW: Differential modification of p27Kip1 controls its cyclin D-cdk4 inhibitory activity. *Mol Cell Biol* 2008, 28:498-510.

(Continued)

*Primary Examiner* — Satyanarayana R Gudibande
(74) *Attorney, Agent, or Firm* — Dority & Manning, P.A.

(57) ABSTRACT

Structural and functional analysis of peptide inhibitor binding to the cyclin D1 groove has been investigated and used to design peptides that provide the basis for structure-activity relationships, have improved binding and have potential for development as chemical biology probes, as potential diagnostics and as therapeutics in the treatment of proliferative diseases including cancer and inflammation.

3 Claims, 4 Drawing Sheets

(56) References Cited

OTHER PUBLICATIONS

Kontopidis G, Andrews MJI, McInnes C, Cowan A, Powers H, Innes L, Plater A, Griffiths G, Paterson D, Zheleva DI, et al.: Insights into cyclin groove recognition: complex crystal structures and inhibitor design through ligand exchange. *Structure* 2003, 11:1537-1546.

Landis MW, Pawlyk BS, Li T, Sicinski P, Hinds PW: Cyclin D1-dependent kinase activity in murine development and mammary tumorigenesis. *Cancer Cell* 2006, 9:13-22.

Liu et al., Structural and Functional Analysis of Cyclin D1 Reveals p27 and Substrate Inhibitor Binding Requirements. ACS Chem Biol 2010, 5(12): 1169-1182.

Malumbres M, Barbacid M: To cycle or not to cycle: a critical decision in cancer. *Nature Reviews Cancer* 2001, 1:222-231.

McInnes C, Andrews MJI, Zheleva DI, Lane DP, Fischer PM: Peptidomimetic design of CDK inhibitors targeting the recruitment site of the cyclin subunit. *Current Medicinal Chemistry—Anti-Cancer Agents* 2003, 3:57-69.

Mendoza N, Fong S, Marsters J, Koeppen H, Schwall R, Wickramasinghe D: Selective Cyan-dependent Kinase 2/Cyclin A Antagonists that Differ from ATP Site Inhibitors Block Tumor Growth. *Cancer Research* 2003, 63:1020-1024.

Oelgeschlager T: Regulation of RNA polymerase II activity by CTD phosphorylation and cell cycle control. *Journal of Cellular Physiology* 2002, 190:160-169.

Ray A, James MK, Larochelle S, Fisher RP, Blain SW: p27Kip1 inhibits cyclin D-cyclin-dependent kinase 4 by two independent modes. *Mol Cell Biol* 2009, 29:986-999.

Russo AA, Jeffrey PD, Patten AK, Massague J, Pavletich NP: Crystal structure of the p27Kip1 cyclin-dependent-kinase inhibitor bound to the cyclin A-Cdk2 complex. *Nature* 1996, 382:325-331.

Schulman BA, Lindstrom DL, Harlow E: Substrate recruitment to cyclin-dependent kinase 2 by a multipurpose docking site on cyclin A. *Proceedings of the National Academy of Sciences of the United States of America* 1998, 95:10453-10458.

Sherr CJ: Cancer cell cycles. Science 1996, 274:1672-1677.

Takaki T, Echalier A, Brown NR, Hunt T, Endicott JA, Noble ME: The structure of CDK4/cyclin D3 has implications for models of CDK activation. *Proc Natl Acad Sci U S A* 2009, 106:4171-4176.

Yu Q, Sicinska E, Geng Y, Ahnstrom M, Zagozdzon A, Kong Y, Gardner H, Kiyokawa H, Harris LN, Stal O, et al.: Requirement for CDK4 kinase function in breast cancer. *Cancer Cell* 2006, 9:23-32.

Cho et al., Journal of Computationla Chemistry, vol. 26, Issue 1, pp. 48-71, 2005.

* cited by examiner

M210 I213 *L214 D216* W217 E220 V221 *E224 R250* G251 L253 Q254 Y280 I281 T282 D283 T285
M56 I59 *V60 T62* W63 E66 V67 *E70 K96* S97 L99 Q100 I126 Y127 T128 D129 S131
FIG. 1A
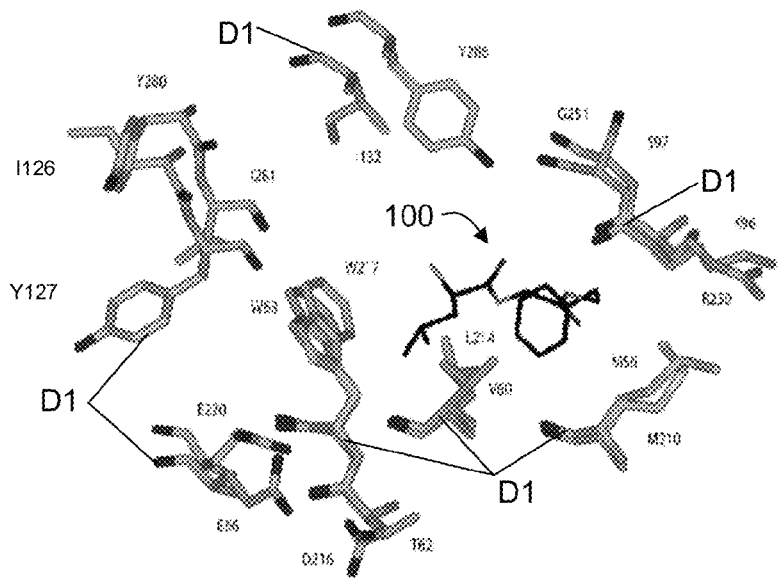
FIG. 1B
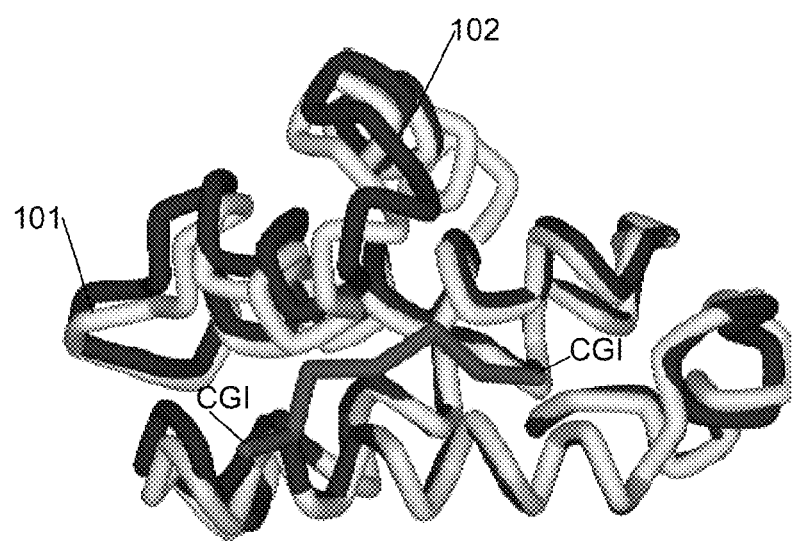
FIG. 1C

SEQUENCE LISTING

<160> NUMBER OF SEQ ID NOS: 38

<210> SEQ ID NO 1

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ala Lys Arg Asn Leu Phe Gly Met
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 2

Ser Ala Lys Arg Arg Leu Xaa Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 3

His Ala Lys Arg Arg Leu Ile Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Leu Ile Phe
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Lys Arg Arg Leu Phe Gly
1               5

<210> SEQ ID NO 6
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Ala Lys Arg Arg Leu Ile Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Val Lys Arg Arg Leu Asp Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cit

<400> SEQUENCE: 8

Xaa Arg Leu Ile Phe
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 2-furylalanine

<400> SEQUENCE: 9

Ser Ala Lys Arg Arg Leu Ala Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 2-thienyl alanine

<400> SEQUENCE: 10

Ser Ala Lys Arg Arg Leu Ala Gly
1               5
```

```
<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 3-thienyl alanine

<400> SEQUENCE: 11

Ser Ala Lys Arg Arg Leu Ala Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cyclobutylalanine

<400> SEQUENCE: 12

Ser Ala Lys Arg Arg Leu Ala Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cyclopentylalanine

<400> SEQUENCE: 13

Ser Ala Lys Arg Arg Leu Ala Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Cyclohexylalanine

<400> SEQUENCE: 14

Ser Ala Lys Arg Arg Leu Ala Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                                peptide
<220> FEATURE:
<221> NAME/KEY: MOD_RES
<222> LOCATION: (7)..(7)
<223> OTHER INFORMATION: 3-pyridylalanine

<400> SEQUENCE: 15

Ser Ala Lys Arg Arg Leu Ala Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 4-pyridylalanine

<400> SEQUENCE: 16

Ser Ala Lys Arg Arg Leu Ala Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 2-furylalanine

<400> SEQUENCE: 17

His Ala Lys Arg Arg Leu Ile Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 2-thienyl alanine

<400> SEQUENCE: 18

His Ala Lys Arg Arg Leu Ile Ala
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-thienyl alanine

<400> SEQUENCE: 19
```

```
His Ala Lys Arg Arg Leu Ile Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cyclobutylalanine

<400> SEQUENCE: 20

His Ala Lys Arg Arg Leu Ile Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cyclopentylalanine

<400> SEQUENCE: 21

His Ala Lys Arg Arg Leu Ile Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cyclohexylalanine

<400> SEQUENCE: 22

His Ala Lys Arg Arg Leu Ile Ala
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-pyridylalanine

<400> SEQUENCE: 23

His Ala Lys Arg Arg Leu Ile Ala
1               5

<210> SEQ ID NO 24
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 4-pyridylalanine

<400> SEQUENCE: 24

His Ala Lys Arg Arg Leu Ile Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4FPhe

<400> SEQUENCE: 25

Arg Arg Leu Ile Phe
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cit

<400> SEQUENCE: 26

His Ala Lys Xaa Arg Leu Ile Phe
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cit

<400> SEQUENCE: 27

Arg Xaa Leu Ile Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
His Ala Lys Thr Arg Leu Ile Phe
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Lys Arg Asn Leu Phe Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ala Lys Arg Ala Leu Phe Gly Met
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Ala Lys Arg Arg Leu Phe Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Val Lys Arg Arg Leu Phe Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 3-chlorophenylalanine

<400> SEQUENCE: 33

Pro Val Lys Arg Arg Leu Phe Gly
1               5
```

```
<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term 3PBA

<400> SEQUENCE: 34

Ser Ala Lys Arg Arg Leu
1               5

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Leu Ile Phe
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 1-(3,5-dichlorophenyl)-5-methyl-1H-
      1,2,4-triazole-3-carbonyl

<400> SEQUENCE: 36

Arg Leu Ile Phe
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Ile Thr Asp
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Tyr Thr Asp
1
```

CYCLIN BASED INHIBITORS OF CDK2 AND CDK4

CROSS REFERENCE TO RELATED APPLICATION

This application is a divisional application of U.S. patent application Ser. No. 13/088,694, now U.S. Pat. No. 8,566,072, having a filing date of Apr. 18, 2011, which claims filing benefit of U.S. Provisional Patent Application Ser. No. 61/342,598 having a filing date of Apr. 16, 2010, which is incorporated herein in its entirety by reference.

GOVERNMENT SUPPORT CLAUSE

This invention was made with government support under RO1 CA131368-O1A2 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 3, 2013, is named USC-279_SL.txt and is 9,950 bytes in size.

BACKGROUND

CDKs, the cyclin regulatory subunits and their natural inhibitors, the CDK tumor suppressor proteins (CDKIs), are central to cell cycle regulation and their functions are commonly altered in tumor cells. Deregulation of CDK2 and CDK4 through inactivation of CDKIs such as $p16^{INK4a}$, $p21^{WAF1}$, $p27^{KIP1}$, and $p57^{KIP2}$ may override the G1 checkpoint and lead to transformation. CDKs interact with certain cell cycle substrates through the cyclin binding motif (CBM) and form a complex with the cyclin groove of the G1 and S phase cyclins, a surface binding site involving a protein-protein interaction. It has been shown that CDK isoform and substrate selective inhibition may be achieved through the use of peptides that block recruitment of both pRb and E2F and potently inhibit CDK2/CA kinase activity. Inhibition of CDKs though the cyclin provides an approach to obtain selectivity against other protein kinases and inhibit only the G1 and S phase CDKs as only these contain a functional cyclin binding groove. In particular, CDKs that regulate the RNA polymerase-II transcription cycle should be unaffected by cyclin groove inhibitory (CGI) compounds. Although it has been shown that cancer cells depend on the RNAPII cycle to express anti-apoptotic genes and that inhibition of transcriptional CDKs leads to potent anti-tumor agents, it is at the same time likely that this will lead to effects in normal cells and may be responsible for toxicities observed with current CDK inhibitors being clinically evaluated.

The cyclin binding motif represents a consensus of the cyclin groove binding sequences found in many cell cycle and tumor suppressor proteins. CGI peptides in transducible form have been shown to induce cell cycle arrest and selective apoptosis in tumor cells in vitro. These permeabilized peptides also act as anti-tumor agents in that when administered directly to a SVT2 mouse tumor model, significant tumor growth inhibition was obtained and histological analysis showed that tumors underwent apoptosis.

The ATP competitive CDK inhibitors developed to date are generally non specific against the single variants in the CDK family. It is believed that a major component of the anticancer activity of CDK inhibitors is through the transcriptional inhibition of CDK7 and 9. While it has been suggested that transcriptional CDK inhibition may be beneficial for cancer therapy, it is also probable that this will lead to significant toxicities. The most selective CDK inhibitor described to date is a CDK4, 6 selective compound, PD0332991 (selective vs. CDK2/protein kinases (CDK4 $IC_{50}$, 0.011 µmol/L; Cdk6 $IC_{50}$, 0.016 µmol/L, no activity against 36 other protein kinases) although it has apparently not been tested against the transcriptional CDKs. Regardless, this compound is a potent antiproliferative agent against retinoblastoma (Rb)-positive tumor cells and induces a G1 arrest, with concomitant reduction of phospho-Ser780/Ser795 on pRb. Oral administration to mice bearing the Colo-205 human colon carcinoma xenografts resulted in marked tumor regression suggesting that it has significant therapeutic potential and that targeting CDK4/cyclin D may be a viable strategy. In addition to cyclins A and E, the D-type cyclins also contain a functional cyclin groove and CDK4/cyclin D dependent kinase activities may therefore be blocked by cyclin groove inhibitors.

Further oncology target validation for selective inhibition of CDK4/cyclin D has been demonstrated using models of breast cancer and where it was shown that mice lacking Cyclin D are highly resistant to mammary carcinomas induced by erbB-2 oncogene. Further research into the role of Cyclin D in tumor formation made use of a mutant form which binds to CDK4/6 but cannot promote catalytic activity. This kinase-defective Cyclin D/CDK complex results in more evidence of resistance to erbB-2 induced tumorigenesis in mice. Combination of these two studies strongly indicates that Cyclin D1/CDK4 kinase activity is required for erbB-2-driven tumorigenesis and therefore confirms that Cyclin D1/CDK4 is a promising oncology target. While there are several reports of potent and selective inhibitors of the CDK2/cyclin A, E substrate recruitment, with both peptidic and peptidomimetic compounds being identified, very little has been reported with respect to either inhibitors or on the requirements for binding to the cyclin groove of CDK4,6/cyclin D1.

SUMMARY

According to one embodiment, disclosed is a method for developing a peptide inhibitor of a complex that may form between a CDK protein and a cyclin D protein. For example, the method may include generating an in silico model comprising a second, different peptide inhibitor bound to a second, different cyclin protein. For instance, the second peptide inhibitor may be a known inhibitor that may inhibit complex formation between the second cyclin protein and a second, different CDK protein.

The method may also include superimposing the first cyclin protein on the in silico model and then deleting the second cyclin protein from the in silico model to form a model of the second peptide inhibitor bound to the first cyclin protein. In addition, the deletion may be carried out in steps such that an energy minimum is converged upon.

The method may also include determining the location of conformation differences between the two models, i.e., the model of the cyclin D protein and the peptide inhibitor and the model of the second cyclin protein and the peptide inhibitor. Based upon the conformation differences, the structure of the peptide inhibitor may be altered to develop a new peptide inhibitor. Beneficially, the affinity of the cyclin D protein to this new peptide inhibitor may be greater than the affinity of the cyclin D protein to the peptide inhibitor used in the modeling simulation.

Also disclosed are peptide inhibitors that may be formed by the method. In general, the peptide inhibitor may include one or more substitutions and/or additions of an amino acid or a synthetic constituent as compared to another CDK/cyclin inhibitor, e.g., the CDK/cyclin inhibitor that is used in the in silica model.

BRIEF DESCRIPTION OF THE FIGURES

FIG. 1A is an alignment of binding site residues of cyclin A2 and cyclin D1 (SEQ ID NOS 37 and 38, respectively, in order of appearance).

FIG. 1B illustrates an overlay of crystal structures of cyclin D1 (marked as D1; 2W96) and cyclin A2 (1OKV) illustrating similarities and differences of CBM contacting residues.

FIG. 1C is a ribbon representation of the overlay highlighting the differences in the cyclin box helices. Cyclin D1 is shown in the lightest strand and the CGI peptide is marked at either end.

DETAILED DESCRIPTION

Figure 2:
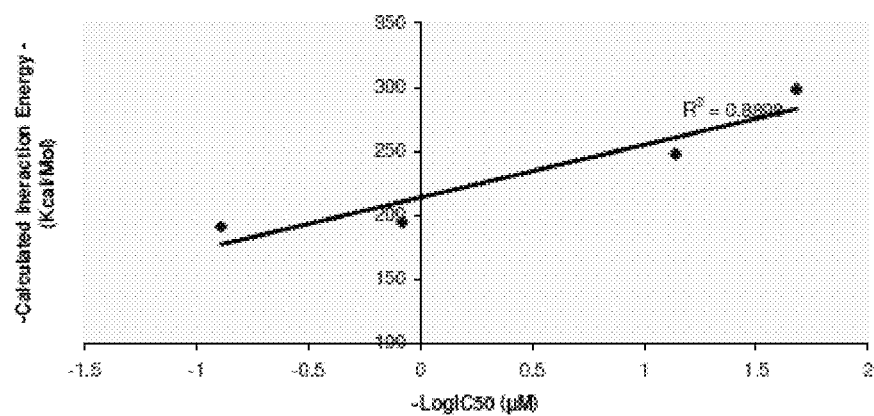
FIG. 2 illustrates a correlation between IC50 and interaction energy for several cyclin A-peptide complexes.

The following description and other modifications and variations to the present subject matter may be practiced by those of ordinary skill in the art, without departing from the spirit and scope of the present disclosure. In addition, it should be understood that aspects of the various embodiments may be interchanged in whole or in part. Furthermore, those of ordinary skill in the art will appreciate that the foregoing description is by way of example only, and is not intended to limit the disclosure.

In general, disclosed herein is a strategy for inhibition of the cyclin dependent kinases in anti-tumor drug discovery. More specifically, inhibition may be afforded through the substrate recruitment site on the cyclin positive regulatory subunit. This approach offers the potential of generating cell cycle specific CDK inhibitors and reduction of the inhibition of transcription mediated through CDK7 and 9, commonly observed with ATP competitive compounds. While highly potent peptide and small molecule inhibitors of CDK2/cyclin A, E substrate recruitment have been reported, little information has been generated on the determinants of inhibitor binding to the cyclin groove of the CDK4/cyclin D1 complex. CDK4/cyclin D is a validated anti-cancer drug target and it continues to be widely pursued in the development of new therapeutics based on cell cycle blockade.

Peptides disclosed herein have been developed from investigation of the structural basis for peptide binding to this cyclin groove and examination of the features contributing to potency and selectivity of inhibitors. Peptidic inhibitors of CDK4/cyclin D of pRb phosphorylation are disclosed, examples of which have been synthesized, and their complexes with CDK4/cyclin D1 crystal structures have been generated as further described herein. Comparisons of the cyclin grooves of cyclin A2 and D1 are presented and provide insights in the determinants for peptide binding and the basis for differential binding and inhibition.

In addition, a complex structure has been generated in order to model the interactions of the CDKI, p27$^{KIP1}$, with cyclin D1. This information has been used to identify unique aspects of cyclin D1 that have a significant impact on peptide interaction, and which may be exploited in the design of cyclin groove based CDK inhibitors. Peptidic and non-peptidic compounds have been synthesized in order to explore structure-activity relationship for binding to the cyclin D1 groove which to date has not been carried out in a systematic fashion. Disclosed compounds may be useful as chemical biology probes to determine the cellular and anti-tumor effects of CDK inhibitors that are cell cycle specific and do not inhibit the transcriptional regulatory effects of other cyclin dependent kinases. Furthermore, such compounds may serve as templates for structure-guided efforts to develop potential therapeutics based on selective inhibition of CDK4/cyclin D activity.

Common amino acid symbol abbreviations as described below in Table 1 are used throughout this disclosure.

TABLE 1

| Amino Acid | One letter symbol | Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Methods
Solid Phase Peptide Synthesis

Peptides were assembled by using standard solid phase synthesis method on a Argonaut Quest 210 semi-automated solid phase synthesizer. 10 equivalents of the C-terminal amino acid were coupled to Rink resin at the first place using DIEA (0.082 ml) and HBTU (189.6 mg) in 5 ml DMF for 1 h. Fmoc of the C-terminus amino acid was removed using 20% piperidine in 5 ml DMF for 10 mins before assembly of 10 equivalents of the next amino acid using DIEA (0.082 ml) and HBTU (189.6 mg) in 5 ml DMF. Wash cycles (5*10 ml DMF+5*10 ml DCM) were applied to each step in between coupling and deprotection of Fmoc. Upon completion of assembly, side chain protecting groups were removed and peptides were finally cleaved from Rink resin using 90:5:5 mixtures of TFA/H$_2$O/TIS. Crude peptides were purified using reverse phase flash chromatography and semi-preparative reversed-phase HPLC methods. Pure peptides were lyophilized and characterized using mass spectrometry and analytical HPLC. All peptides contained free amino termini and were C-terminal carboxamides.

Computational Chemistry

Modeled complexes of peptidic cyclin groove inhibitors bound to either Cyclin A or Cyclin D were generated as follows: SAKRRLXG (SEQ ID NO: 2) series were modeled from the crystal structure the p107 peptide bound to cyclin A (PDB: 1H28). The HAKRRLIX (SEQ ID NO: 3) series were obtained by hybridizing the peptide conformation of RRLIF (SEQ ID NO: 4) (PDB: 1OKV) and SAKRRLFG (SEQ ID NO: 5) (PDB: 1H28). The Cyclin A structure in this complex was taken from 1OKV. Cyclin D1/SAKRRLXG (SEQ ID NO: 2) and Cyclin D/HAKRRLIX (SEQ ID NO: 3) were generated in a similar manner using cyclin D1 crystal structures (PDB: 2W96) where the peptidic inhibitor bound to Cyclin A was superimposed with cyclin D1 and followed by deletion of Cyclin A from further minimization of the complex. After applying the CHARMm forcefield in Discovery Studio 2.5 (Accelrys, San Diego), the Smart Minimizer algorithm comprised of steepest descent and conjugate gradient and an implicit solvent model of Generalized Born with a simple Switching (GBSW) were applied to the complex. In general, all peptide residues were flexible. For cyclin A, all protein residues were restrained and for cyclin D1, the backbone atoms were fixed and approximately 300 steps of minimization were required for convergence to an energy minimum. The calculate interaction energy protocol of DS 2.5 was used to generate non-bonded energy values between peptidic inhibitor and its associated cyclin. This included calculation of van der Waals and electrostatic energies to provide an estimation of the affinity of inhibitors In Vitro Kinase Assay CDK2/Cyclin A2 and CDK4/Cyclin D1 kinase assays were performed using full-length recombinant CDK2/cyclin A2 and CDK4/Cyclin D1 co-expressed by baculovirus in Sf9 insect cells using an N-terminal GST tag on both proteins. The kinase assay buffer I consisted of 25 mM MOPS, pH7.2; 12.5 mM beta-glycerol-phosphate, 25 mM $MgCl_2$, 5 mM EGTA, 2 mM EDTA and 0.25 mM of DTT was added prior to use. The [$^{32}$P]-ATP Assay cocktail was prepared in a designated radioactive working area by adding 150 ul of 10 mM ATP stock solution, 100 ul[$^{32}$P]-ATP (1 mCi/100 ul), 5.75 ml of kinase assay buffer I. 10 mM ATP Stock Solution was prepared by dissolving 55 mg of ATP in 10 ml of kinase assay buffer I. Store 200 µl aliquots at −20° C. The substrate used is Rb (773-928) protein with 0.2 mg/ml concentration. The blank control was set up by adding 10 µl of diluted active CDK/Cyclin with 10 µl of distilled $H_2O$. Otherwise, adding 10 µl of diluted active CDK/Cyclin with 10 µl of 0.2 mg/ml stock solution of Rb (773-928). The reaction was initiated by the addition of 5 µl [$^{32}$P]-ATP assay cocktail bringing the final volume up to 25 µl and incubating the mixture in a water bath at 30° C. for 15 minutes. After the incubation period, the reaction was terminated by spotting 20 µl of the reaction mixture onto individual pre-cut strips of phophocellulose P81 paper. The pre-cut P81 strip was air-dried and sequentially washed in a 1% phosphoric acid solution with constant gentle stirring. Radioactivity on the P81 paper was counted in the presence of scintillation fluid on a scintillation counter. The corrected cpm was determined by subtracting the blank control value for each sample and calculating the kinase specific activity as follows: Calculation of [$P^{32}$]-ATP specific activity (SA) (cpm/pmol) Specific activity (SA)=cpm for 5 ul [$^{32}$P]-ATP/pmoles of ATP (in 5 ul of a 250 uM ATP stock solution). Kinase Specific Activity (SA) (pmol/min/ug or nmol/min/mg) Corrected cpm from reaction/[(SA of $^{32}$P-ATP in cpm/pmol)*(Reaction time in min)*(Enzyme amount in ug or mg)]*[(Reaction Volume)/(Spot Volume)] (SignalChem, Richmond, Canada)

Results

Structural Comparison of Cyclin A2 and D1 Binding Grooves

While numerous experimental structures exist for CDK2/cyclin A2 and other cyclin structures have been solved, for many years CDK4 in complex with the D type cyclins proved refractory to crystallization. The structures for CDK4 in complex with cyclin D1 were recently solved however only in complex with ligands binding to the ATP cleft. This data provided the opportunity to gain new insights into the cyclin groove of the D cyclins and also to determine the basis for their interactions with cyclin groove inhibitory (CGI) peptides. At the outset of this study, a limited body of data had been generated for CDK4 inhibition where a series of peptides explored biologically as CDK2/cyclin A, E inhibitors were also characterized in terms of their inhibition of cyclin D1 mediated substrate recruitment. These results determined that highly potent peptidic CDK2 inhibitors were in general, significantly less potent against CDK4.

In order to determine the structural and functional differences of these compounds, their interactions with the cyclin D1 recruitment site were modeled and compared with known cyclin A complex structures. In terms of cyclin A binding, optimized peptides (i.e. the octamer, HAKRRLIF, p21 sequence (SEQ ID NO: 6)) contain three major determinants which are required for high affinity binding. As illustrated in FIG. 1A, these include a primary hydrophobic pocket which interacts predominantly with leucine and phenylalanine residues of the peptide, an acidic region which forms ionic contacts with basic peptide residues and a secondary hydrophobic pocket occupied by either an alanine or valine of the cyclin binding motif (CBM). While the majority of CGI peptide contacting residues are identical or semi-conserved in both cyclin isotypes, two notable exceptions were observed. In cyclin D1, Val60 (interacts with Phe8) and Thr62 (close to Arg4) are substituted for Leu214 and Asp216 in cyclin A2 respectively. As these residues in the cyclin A context, make contacts with major determinants of cyclin A binding, it is expected that even semi-conservative replacements would lead to significant effects on cyclin groove inhibition.

Upon overlay of the corresponding alpha carbons of the two cyclins, other semi-conserved and non-conservative differences were observed in the structural comparison. These residues are not as significant for binding of the octapeptide however their proximity to the cyclin binding groove suggests that they have potential for exploiting in the design of selective CDK inhibitors targeting cyclin D1. Of the non peptide contacting residues, the largest structural variation is in the exchange of Y286 of cyclin A for I132 of cyclin D1. Overlay and comparison of the Calpha trace of the two structures indicates that this variation, coupled with the relative movement of a helix-loop segment (residues 119-136 of 2W96) leads to a significant conformation variation proximal to the cyclin groove. This region as a consequence is considerably more open in cyclin D1 and provides an extension to the primary hydrophobic pocket. This additional pocket could therefore accommodate larger ligand groups than would be feasible for cyclin A inhibitors.

Sequence alignment of binding sites for cyclin A2 (top) and cyclin D1 (bottom) are shown in FIG. 1A. Residues that contribute to selectivity are shown in italics. The alignment reveals that while a majority of the residues are conserved, Leu214/Val60, Asp216/Thr62, Glu224/Glu70, and Arg250/Lys96 are the main residues that are responsible for selectivity.

FIG. 1B illustrates an overlay of crystal structures of cyclin D1 (2W96) and cyclin A2 (1OKV) illustrating similarities and differences of CBM contacting residues. The Leu and Phe residues of the CBM interacting with the primary hydrophobic pocket are shown at 100. E220 and D216 comprise the acidic region and the secondary hydrophobic pocket is to the left of W217.

FIG. 1C is a ribbon representation of the overlay highlighting the differences in the cyclin box helices. Cyclin D1 is shown as the light ribbon and the ends of the CGI peptide are marked. The region displaying the largest structural differences after superimposing the backbone atoms is marked between 101 and 102 (residues 116-136 of cyclin D1).

Another consequence of the differing conformation and composition of the 116-136 region affects the secondary hydrophobic pocket with which the CGI peptide Ala2 interacts. I281 of cyclin A2 is a Tyrosine residue (Y127) in D1. The kinked helix containing this residue is shifted towards the groove, bringing this residue closer to the peptide and decreasing the volume of the lipophilic pocket on the peptide N-terminal side of the W63 (FIG. 3B).

Structural Basis for Cyclin D1 Inhibition

Prior to detailed analysis of modeled peptide-cyclin D1 complexes, the structural and energetic basis for potencies of cyclin A inhibitors was examined. Since a complete set of cyclin A crystal structures for peptides with cyclin D1 affinity is not available, a cyclin A complex for HAKRRLIF (SEQ ID NO: 6) was first constructed. This peptide is highly selective for cyclin A versus cyclin D1. Formation was completed by building on existing pentapeptide (1OKV) and octapeptide structures to supplement those available for PVKRRLDL (E2F) (SEQ ID NO: 7) and SAKRRLFG (p107) (SEQ ID NO: 5) CBM sequences. The non-bonded interactions of these crystallographic complexes were estimated by calculation of per residue and total interaction energy values (DS 2.5, Accelrys) to determine individual contributions and to establish if these were reflective of the observed affinities (approximated by inhibition constants). These values shown in Table 2, below, delineated a relationship in terms of both previous SAR of individual residues and CGI potency.

both HAKRRLIF (SEQ ID NO: 6) and RRLIF (SEQ ID NO: 4) calculated (−298 vs −188) correlate well with the inhibition constants of these two compounds. Further analysis of the cyclin residue energetics determined that acidic residues, including Asp216, Glu220, Glu224 and Asp283 allow favorable electrostatic contacts with the basic peptide N-terminal sequence. In addition, the energetics of the contribution of Ala2 to binding correlates well with observed potency increase of the Ser-Ala mutation in the p21 C-terminal context.

Further correlation of the interactions and contributions of the C-terminal sequence of the CBM interacting with the primary hydrophobic pocket (FIG. 1A) in addition to visual inspection of the non-bonded contacts in the p21, p107 and E2F contexts, indicates the structural and energetic differences. In varying peptide sequence contexts, the p21 Leu-Ile-Phe (LIF 'motifette') sequence has been demonstrated to be more potent than the p107 (and p27) LFG and E2F, LDL motifettes. Table 2 illustrates that while the Leucine contributions in each context are similar, the Phe side chain provides increased complementarity in the p21 sequence (−23.5 kcal/mol vs. −12.2) resulting in its 2-3 fold greater affinity compared to the LFG sequence. More favorable contacts are observed due to the geometrical arrangement of the aromatic side chain allowed by the spacer residue between the Leu and Phe in the p21 context. Overall, the energetic analysis of peptide binding to cyclin A confirms that a relationship exists between calculated binding enthalpy and experimental affinity and additionally that individual residue energetics closely

TABLE 2

(SEQ ID NOS 6, 5, 7, 4, 8, 6, 5, 7, 4 and 8, respectively, in order of appearance)

| | Cyclin A | | Cyclin A | | Cyclin A | | Cyclin A | | Cyclin A |
|---|---|---|---|---|---|---|---|---|---|
| H | −65.1 | S | −63.9 | P | −23.1 | | | | |
| A | −18.0 | A | −19.2 | V | −15.8 | | | | |
| K | −42.2 | K | −40.6 | K | −47.4 | | | | |
| R | −72.3 | R | −69.7 | R | −74.3 | R | −111.3 | Cit | −38.4 |
| R | −58.7 | R | −25.2 | R | −9.3 | R | −46.4 | R | −47.2 |
| L | −11.7 | L | −12.8 | L | −9.9 | L | −13.8 | L | −13.8 |
| I | −6.8 | F | −12.2 | D | 0.6 | I | −0.1 | I | −0.06 |
| F | −23.5 | G | −4.2 | L | −15.4 | F | −19.5 | F | −19.6 |
| total | −298.3 | | −247.8 | | −194.6 | | −191.1 | | −119.06 |
| | Cyclin D | | Cyclin D | | Cyclin D | | Cyclin D | | Cyclin D |
| H | −20 | S | −24.1 | P | −18.8 | | | | |
| A | −6.3 | A | −5.6 | V | −11.9 | | | | |
| K | −44.6 | K | −44.7 | K | −52.2 | | | | |
| R | −54.7 | R | −57 | R | −47.6 | R | −106.9 | Cit | −30.3 |
| R | −27 | R | −17.6 | R | −11.1 | R | −19.2 | R | −19.2 |
| L | −15.2 | L | −13.7 | L | −14.7 | L | −14.1 | L | −14.1 |
| I | 0.7 | F | −10.2 | D | −1.6 | I | 0.2 | I | 0.2 |
| F | −13 | G | −4.7 | L | −11.7 | F | −13.9 | F | −13.9 |
| TOTAL | −180.1 | | −177.6 | | −169.6 | | −153.9 | | −77.3 |

As determined through sensitivity to major potency loss by alanine substitution and other residue replacement, as shown, the energetic analysis shows the critical Arg4 of the octapeptide makes an extensive contribution to binding, whereas that of the less sensitive Arg5 is lower. Truncation of the His-Ala-Lys N-terminal sequence has been previously shown to result in a decreased affinity for cyclin A with the potency decreasing approximately 100 fold. The contribution of these three residues to binding is confirmed through the energetic analysis where His1 and Lys3 especially provide favorable interactions with the binding pocket. The total binding energies of correlate with the SAR and contribution of CBM determinants. This relationship provides the basis to perform an analysis of peptide binding to cyclin D1 and to determine the structural basis for decreased affinity of cyclin D1 inhibitors and therefore to facilitate the design of more potent compounds.

The intermolecular complexes of cyclin D1 with the above peptides were formed by superposition of the apo-cyclin D1 structure (2W96) with the crystallographically derived cyclin A bound structure of the CBM containing peptides and followed by deletion of cyclin A. The energy-minimized structure was then calculated using the CHARMm molecular forcefield, and the similarities and differences of cyclin binding motif-cyclin interactions were examined.

In order to further probe the molecular consequences of variations in binding residues, the intermolecular energies were calculated for the interactions of each of the peptides with cyclins A and D1. In line with the observed potencies of each compound and selectivity for cyclin A, a correlation was determined between affinity (kinase inhibition) and total interaction energy (CIE) calculated for 4 peptides ranging in $IC_{50}$ from 0.021 to 99 μM. Results are illustrated in Table 3, below and FIG. 2.

TABLE 3

| Cyclin A | SEQ ID NO: | Interaction Energy (Kcal/Mol) | IC50 (μM) | LogIC50 |
|---|---|---|---|---|
| HAKRRLIF | 6 | −298.3 | 0.021 | −1.68 |
| SAKRRLFG | 5 | −247.8 | 0.073 | −1.14 |
| PVKRRLDL | 7 | −194.6 | 1.2 | 0.08 |
| RRLIF | 4 | −191.1 | 7.7 | 0.89 |

For this relationship, an $R^2$ of 0.91 indicated that the both the crystal and modeled structural complexes were accurate and that the established correlation is useful as a predictive tool for design and synthesis of more potent and selective compounds. Comparison of the predicted affinities of each peptide also demonstrated that the CIE correlates well with the selectivity of the compound for cyclin A (Table 2). This was additionally confirmed by a second method for estimation of binding affinity. Calculation of Ludi Scores provided results directly in line with the relative potencies on A vs. D1. Further analysis of the individual energetic contributions of residues of both the peptide and cyclin in each context revealed further evidence for the structural basis of CGI selectivity. Not surprisingly, it was observed that the cyclin D binding site variations described above contributed extensively to the selectivity of each peptide for cyclin A2. Of course, any inhibitory peptide may be utilized in a modeling process as disclosed herein. In general, the peptide inhibitor will be relatively short, for instance about 10 amino acids or less in length, or about 8 amino acids or less in length, such as the octapeptides, pentapeptides, and tetrapeptides specifically detailed herein.

The optimized p21 derived peptide, HAKRRLIF (SEQ ID NO: 6) is highly selective for A (0.021 μM) vs. D1 (6 μM). In addition to the total interaction energy describing the non-bonded interactions of the peptide-cyclin interaction, the individual contributions of residues from both molecules was determined. These results indicate that the highly basic N-terminal residues interact much more favorably with the cyclin A groove. As no crystal structure is available for this peptide, an A complex was modeled on the basis of the residue contacts of RRLIF (1OKV) (SEQ ID NO: 4) and SAKRRLFG (1H28) (SEQ ID NO: 5). Analysis of protein-peptide contacts and interaction energies reveals that a greater concentration of acidic residues in A2 compared to D1 contributes extensively to this selectivity. In particular Asp216 of cyclin A2 (which is aligned with T62 of cyclin D1) provides a favorable addition of 17 kcal/mol to the binding energy in interactions with Arg4. This contribution is largely absent in the cyclin D1 complexes modeled where the hydroxyl group of T62 weakly interacts with Arg4. When the interaction of both Arg4 and Arg5 are considered, the calculated binding energy of these two residues for cyclin A is more than twice that observed for cyclin D1. Glu220 in Cyclin A2 interacts with Arg4 similarly to the corresponding residue (Glu66) in Cyclin D suggesting that the energetic differences are mainly due to the absence of the second acidic residue in D.

As mentioned above, comparison of the CGI peptide binding residues in cyclin D1 revealed that a valine residue occupied the position observed as a leucine in A2 (Leu214Val). As this residue is located in the lipophilic pocket interacting with the LIF motif of p21, the immediate conclusion is that this contributes significantly to peptide selectivity for A vs D. Initially, this appears to be counterintuitive since valine is a smaller residue and might be expected to provide a larger binding pocket. Close examination of the position of Val60 indicates that the shorter and less flexible side chain brings the interacting methyl groups closer to the phenylalanine of the peptide and therefore decreases the volume of the hydrophobic pocket (FIGS. 1B, 3B). This was confirmed upon overlay of cyclin A2 bound to HAKRRLIF (SEQ ID NO: 6) with the cyclin D1 modeled complex, where a significant steric clash with the Phe8 side chain was observed (FIGS. 1A, 1B). This suggests that the binding mode of Phe8 with cyclin A2 is not compatible for interaction with cyclin D. In order to determine the consequences of the overlap, the complex formed between cyclin D1 and HAKRRLIF (SEQ ID NO: 6) was subjected to energy minimization to relieve this overlap. A significant displacement of the phenylalanine was observed and which did not come at the expense of Leu6 (peptide residue), whose position was not affected. Further analysis of the interaction energy and comparison with the values calculated for octapeptide inhibition of both cyclins, indicated a reasonable correlation between predicted and calculated per-residue affinity of the C-terminal motifette. These data suggest that displacement of the aromatic side chain comes at the expense of its complementarity with the primary hydrophobic pocket and that the valine substitution is responsible for the significant decrease in affinity for cyclin D1.

Figure 3:
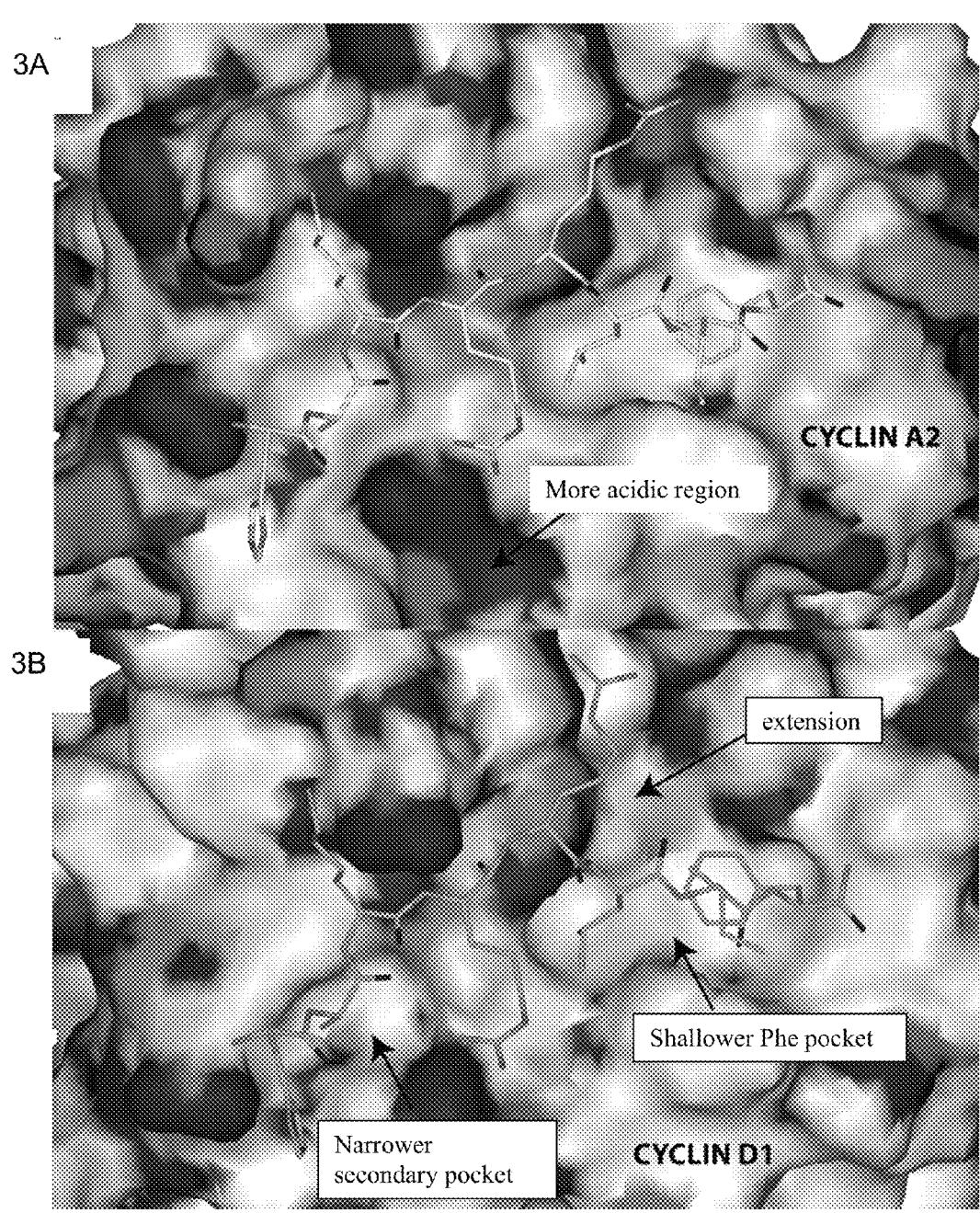
FIG. 3 is a comparison of the solvent accessible surface of the cyclin grooves of A2 (FIG. 3A) and D1 (FIG. 3B).

FIG. 3 is a comparison of the solvent accessible surface of the cyclin grooves of A2 (FIG. 3A) and D1 (FIG. 3B). The individual subsites of the CBG are labeled for each cyclin. Examination of the intermolecular contacts and interaction energies for SAKRRLFG (p107 cyclin binding motif) (SEQ ID NO: 5) with cyclin D1 reveals a similar pattern of residue energetics for the basic region of the peptide as in the HAKRRLIF (SEQ ID NO: 6) context. SAKRRLFG (SEQ ID NO: 5) has a lower affinity for cyclin A, with the less optimal geometry of the LFG motifette resulting in a reduced contact surface area of the phenyl ring with the pocket. Calculation of the individual residue interaction energies suggests that the presence of Val60 has a markedly smaller impact on affinity of the p107 peptide for cyclin D1 than in the p21 context due to the different approach angle of the interacting side chain, and that the selectivity results from increased affinity of the Arg4Arg5 determinant with cyclin A2.

Comparison of the E2F CBM, PVKRRLDL (SEQ ID NO: 7) (Table 3, FIG. 3) reveals further insights into the structural basis for CGI selectivity for cyclin A and after comparison of the binding energetics again indicates less favorable contacts with the peptide in the cyclin D1 context (Table 2). As has been previously described, the LDL containing inhibitors generally have a decreased binding relative to the LIF compounds and in this case is reflected in the 50 fold increased IC50 value. In contrast to the LFG sequence, the LDL sequence has a substantially lower predicted affinity for hydrophobic pocket of cyclin D1, consistent with the observed inhibition constants.

Further Analysis of Peptide SAR and Insights into the Design of Selective Cyclin D1-CDK4 Inhibitors The insights into the structural basis for peptide recognition for cyclin A and for the decreased potency against cyclin D1, provided further opportunity to expand inhibitor structure activity relationships by including additional derivatives. As suggested from the above structural analysis, differences in the primary hydrophobic pocket were the major determinants in cyclin A selectivity of the studied peptides. These observations predicted that analogs with variant C-terminal groups may interact with the cyclin D pocket with differing affinity than to the cyclin A groove. Based on this observation, further peptides were designed to exploit these structural differences and generate compounds with increased affinity for cyclin D1. Due the decreased volume of the primary pocket in cyclin D1, a series of non-proteinogenic cyclic replacements for Phe7 (p107) and Phe8 (p21) cyclin binding motif containing octapeptides were designed. A series of 5 and 6 membered ring systems were incorporated into the p21 (HAKRRLIX (SEQ ID NO: 3)) and p107 (SAKRRLXG (SEQ ID NO: 2)) contexts (Table 4, below). As shown, these included 2-furylalanine (X1), 2-thienyl alanine (X2), 3-thienylalanine (X3), cyclobutylalanine (X4), cyclopentylalanine (X5), cyclohexylalanine (X6) and 3 and 4 pyridyl alanine residues (X7 and X8) providing for the most part isosteric functionalities mimicking the interactions of the phenylalanine.

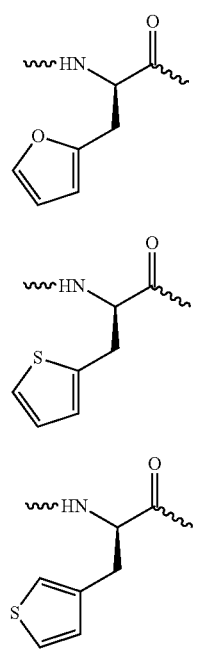

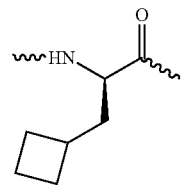

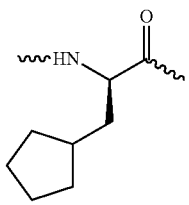

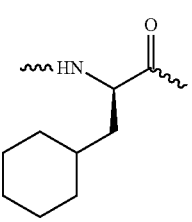

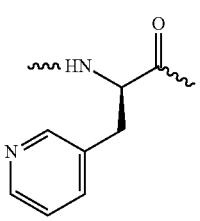

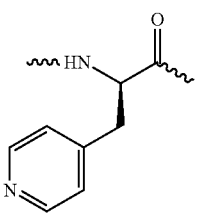

The inhibition of CDK activity was determined through a standard filter capture assay involving a GST-labeled Rb protein and quantification of the incorporation of 32P into the substrate. Activities of peptides previously tested against CDK2A and CDK4D were determined using this assay format. Although similar constructs and substrate was used, significant differences in potency were observed. In particular the IC50 for HAKRRLIF (SEQ ID NO: 6) was approximately 10 fold higher than previously determined (1.3 vs. 0.14 µM) and the inhibition of CDK4/D1 was more pronounced than before (1.6 vs. 6 µM). These differences may be accounted for in slight differences in amount of cyclin in the protein prep and excess cyclin or CDK would result in data variation. As a consequence, it was decided that structure-activity relationships determined using the kinase assay were best interpreted by functional comparisons calculated relative to the native p21 or p107 sequence in each assay. Data is therefore presented as a ratio of each C-terminal and other analogs activity in addition to the IC50s presented for each compound. Results are shown in Table 4, below.

TABLE 4

|  | SEQUENCE | SEQ ID NO: | IC50 CDK2/A2 (μM) | Potency ratio | IC50 CDK4/D1 (μM) | Potency ratio | IC50 CDK2/E (μM) |
|---|---|---|---|---|---|---|---|
| p107 | SAKRRLFG | 5 | 3.3 | | 2.9 | | |
| | SAKRRLX1G | 9 | 9.1 | 2.8 | 7.5 | 2.6 | 4 |
| | SAKRRLX2G | 10 | 27 | 8.2 | 11.4 | 3.9 | |
| | SAKRRLX3G | 11 | 1 | 0.3 | 6 | 2.1 | |
| | SAKRRLX4G | 12 | 100 | 30.3 | 74 | 25.5 | |
| | SAKRRLX5G | 13 | 18 | 5.5 | 28 | 9.7 | |
| | SAKRRLX6G | 14 | 83 | 25.2 | 36 | 12.4 | |
| | SAKRRLX7G | 15 | 80 | 24.2 | 51 | 17.6 | |
| | SAKRRLX8G | 16 | 750 | 227.3 | 143 | 49.3 | |
| p21 | HAKRRLIF | 6 | 1.3 | | 1.5 | | 0.3 |
| | HAKRRL1X1 | 17 | 6.1 | 4.7 | 11.4 | 7.6 | 1.3 |
| | HAKRRLIX2 | 18 | 3.6 | 2.8 | 6.5 | 4.3 | |
| | HAKRRLIX3 | 19 | 25 | 19.2 | 100 | 66.7 | |
| | HAKRRLIX4 | 20 | 25 | 19.2 | 100 | 66.7 | |
| | HAKRRLIX5 | 21 | 20 | 15.4 | 90 | 60.0 | |
| | HAKRRLIX6 | 22 | 58 | 44.6 | 6.3 | 4.2 | |
| | HAKRRLIX7 | 23 | 29 | 22.3 | 28 | 18.7 | |

For the 2-furylalanine replacement (X1) in the p107 context, it was found that kinase activity induced by this compound decreased a similar amount in both CDK2A (2.8 fold) and CDK4D (2.6 fold) although slightly less so for the latter. In the p21 context more of a differential was observed (4.7 and 7.6 fold decrease respectively). The p107 X2 derivative (2-thienylalanine) data indicates that the potency decrease against cyclin D was considerably reduced (3.9 fold) relative to cyclin A (8.2 fold decrease). A similar differential was observed for the p21 X2 derivative (2.8 vs. 4.3 fold respectively). The X3 amino acid, 3-thienylalanine was found to be less potent than X2 in both p107 and p21 contexts.

Examination of the results for aliphatic cyclic amino acid replacements, including cyclobutyl (X4), cyclopentyl (X5) and cyclohexylalanine (X6), indicated that depending on the CBM context, different selectivity profiles were observed. X4 resulted in dramatic potency decreases in both contexts however significantly more so with cyclin A, Both the p21 and p107 versions incorporating X5, indicate that it is tolerated to a larger degree in binding to cyclin A. Conversely, the p21 derivative of X6 is tolerated to a significantly larger degree in binding to cyclin D1 with only a 4 fold drop-off observed compared to 45 fold with CDK2/cyclin A. If the IC50s of this compound are considered, it is significantly more potent towards CDK4/cyclin D1 than against CDK2/cyclin A (6.3 vs. 58 μM). A similar trend was shown for the p107 X6 sequence although was not as dramatic. An interesting set of results was obtained for the pyridylalanine derivatives where one carbon of the native Phe residue is replaced with nitrogen. A large decrease in activity was observed for these compounds in both p21 and p107 variants. Binding to cyclin D1 for these analogs was again tolerated to a larger degree, especially with the 3-pyridylalanine derivative (X7) in the p107 context. Unexpectedly, the activity of 4-pyridylalanine (X8) incorporated in SAKRRLXG (SEQ ID NO: 16) decreases 200 fold relative to the native sequence in terms of cyclin A but 46 fold in the p21 X8 derivative. Further analysis of the p21 analog binding to cyclin D1 indicates that the X8 containing peptide loses all activity towards CDK4/cyclin D1. The binding of X7 to cyclin D1 decreases 17.6 fold relative to the phenylalanine in the LXG motif and 18.7 fold in the LIX context.

Structure-Activity Relationship for Peptide Binding to Cyclin D1

For the CDK4/cyclin D1/pRb SAR of the Phe replacements in the SAKRRLXG (SEQ ID NO: 2) context, the most potent analog is the furylalanine, X1 derivative with an IC50 of 7.5 μM with X2, the 2-thiophene containing peptide being slightly less potent (11.4 μM). The order of potency is reversed in the p21 CBM since HAKRRLIX2 peptide (SEQ ID NO: 18) has approximately 2 fold greater inhibition than the furylalanine containing peptide (6.5 and 11.4 μM respectively). The 3-thienyl analog X3 undergoes a potency drop off relative to X2 in both contexts. Cyclobutylalanine incorporation into the p107 context retained a level of binding as do HAKRRLIX5 (SEQ ID NO: 21) and SAKRRLX5G (SEQ ID NO: 13) although this is weak relative to the native sequences. The cyclohexylalanine replacement, X6 was of equivalent potency to the thiophene containing peptide in the HAKRRLIX context (SEQ ID NO: 22), however of notably higher inhibition than the p107 derivative (6.3 μM vs 36 μM). The 3-pyridylalanine peptides (X7) were considerably more significant inhibitors when incorporated C-terminal to the Ile containing spacer residue and which has previously been shown to allow more favorable geometry for binding. The 4-substituted derivative (X8) are weaker binders in both CBM contexts however with 143 µM IC50 observed in the CDK4/cyclin D1 kinase assay for SAKRRLX8G (SEQ ID NO: 16) and no observable activity for HAKRRLIX8 (SEQ ID NO: 24). For the most part, the p21 sequences follow the previously observed trend as being more potent than the p27 and p107 peptides. Two C-terminal analogs however have higher affinity when incorporated with the p107 residues, these being the furylalanine (X1) and 4-pyridylalanine (X8) containing peptides.

Additional insights into cyclin groove interactions in cyclin D1 are provided by C-terminal and other derivatives incorporated into HAKRRLIF (SEQ ID NO: 6). The p-fluorophenylalanine (4FPhe) derivative has been previously shown to significantly increase the inhibitory potential of peptide cyclin A inhibitors with respect to the native residue. In contrast to these results, synthesis and testing of RRLI (4FPhe) (SEQ ID NO: 25) resulted in decreased inhibition of CDK4/cyclin D1 kinase activity (compared to HAKRRLIF (SEQ ID NO: 6), a 160 fold decrease) vs. only a 20 fold decease in CDK2/cylin A activity).

As discussed in above sections, there are differences in the Arg4 interacting residues in cyclin D1 vs. cyclin A2 and that these variations contribute to decreased binding of peptides to cyclin D1. Specifically, cyclin A has two acidic residues that interact with the positively charged side chain compared to only one in cyclin D1. This residue has previously been shown to be critical for cyclin A binding activity. It would therefore be predicted that replacement of the Arg with an isosteric residue would have less of an impact on cyclin D binding. Incorporation of citrullene into p21 to generate peptide, HAKCitRLIF (SEQ ID NO: 26) in order to determine effect on inhibition of cyclin D confirmed that Arg4 is significant for interaction with cyclin D1, as shown in Table 5. The ratio the activities of the Cit and Arg containing peptides in both contexts revealed that its effect on cyclin D1 activity (14 fold potency decrease) was similar to that observed in cyclin A. This result was corroborated by comparison of the activities of citrullene incorporated into pentapeptide, RCitLIF (SEQ ID NO: 27). Compared to the octapeptide sequence, the 5mer potency decreased roughly 120 fold for cyclin A (1.3 vs. 164 µM) and cyclin D1 (1.5 vs. 179 µM).

TABLE 5

| SEQUENCE | SEQ ID NO: | IC50 CDK2/A2 (µM) | Potency ratio | IC50 CDK4/D1 (µM) | Potency ratio |
|---|---|---|---|---|---|
| SAKRRLFG | 5 | 3.3 | | 2.9 | |
| HAKRRLIF | 6 | 1.3 | | 1.5 | |
| RRLIpfF | 25 | 26 | 20.0 | 250 | 166.7 |
| HAKCitRLIF | 26 | 18 | 13.8 | 21 | 14.0 |
| HAKTRLIF | 28 | 50 | 38.5 | 25 | 16.7 |
| CitRLIF | 8 | 164 | 126.2 | 179 | 119.3 |
| SCCP10 | | 25 | 19.2 | 8 | 5.3 |
| SCCP 5624 | | >100 | | 60 | 20.7 |
| SAKRNLFGM | 1 | | | 146 | |
| SAKRNLFG | 29 | | | 75 | |
| SAKRALFGM | 30 | | | 68 | |
| PAKRRLFG | 31 | 8 | | 6.7 | |
| PVKRRLFG | 32 | 3 | | 28 | |
| PVKRRL3CFG | 33 | 1 | | 3.2 | |

Insights into SAR for interaction of cyclin D1 inhibitors of the secondary hydrophobic was revealed through synthesis of peptides containing the E2F and p107 CBMs. A preference for smaller side chains was indicated by the increased inhibition of PAKRRLFG (SEQ ID NO: 31) compared to that of PVKRRLFG (SEQ ID NO: 32). This result is in agreement with the structural analysis which shows a decreased volume of this subsite in cyclin D1 compared to A From previous studies into the replacement of peptide determinants with fragment alternatives, compounds were identified where the p21 LIF motif was replaced with a Leu-bis-aryl ether system, while maintaining a similar potency level for cyclin A2 inhibition. A compound was synthesized incorporating 3-phenoxybenzylamide replacing the Phe and also N-terminally capped with 1-(3,5-dichlorophenyl)-5-methyl-1H-1,2,4-triazole-3-carboxylic acid and subsequently tested for inhibition of CDK4/D1 (SCCP10 on Table 5). SCCP10 was found to have a respectable inhibition of cyclin D1 and in addition, its relative potency compared to the p21 octapeptide was enhanced compared to cyclin A inhibition. SCCP10 is 5 fold less potent than HAKRRLIF (SEQ ID NO: 6) towards cyclin D1, however undergoes a 20 fold drop off when cyclin A2 activity is considered. A similar trend was observed for the SAKRRL-3PBA peptide (SEQ ID NO: 34) small molecule hybrid 3-phenoxybenzylamide end capped peptide when tested against both cyclin grooves although in this context the cyclin A differential was not as profound. Arg-Arg-β-homoleucyl-3-phenoxybenzylamid (SCCP 5624) was also synthesized and shown to be selective for CDK4/cyclin D1.

The Phe side chain of the octopeptide HAKRRLIF (SEQ ID NO: 6) was replaced with smaller side chains in a series of compounds as shown below in Table 6. SCCP396, possessing furyl-Ala replacement was indeed selective for cyclin D1 (15% of kinase activity enhancement for cyclin D1 vs. A2). Other replacements with larger ring systems (SCCP 397, 401, 402) were not as favorable. The smaller side chains thus reacted more favorably with cyclin D1.

Based upon the above results and other known compounds (see, e.g., Andrews, et al. ChemBioChem, 2006, 7, 1909-1915), the N-terminal Arginine of the p21 RLIF tetrapeptide (SEQ ID NO: 35) was substituted with a series of different heterocyclic isosteres capable of interactions similar to critical amino acids of the parent peptide and the triazole. Pyrazole, furan, pyrrole and thiazole systems were synthesized and various substitutions of the phenyl ring were explored. The N-caps were ligated to the tetra peptide using solid phase synthesis, purified by reverse phase HPLC and characterized by MS.

In vitro binding and functional assays were performed in order to study the inhibitory effect of compounds on CDK2/Cyclin A prior to further evaluation in cell viability assays to determine antitumor effects. On the basis of the results, further high throughput docking of potential heterocyclic fragments was carried out to identify N-capping groups of varying chemical diversity for synthesis and in vitro testing.

The triazole core structure of 1-(3,5-dichlorophenyl)-5-methyl-1H-1,2,4-triazole-3-carbonyl was replaced with isosteres such as pyrazole, furoic acid, pyrrole, and thiazole appropriately substituted with a carboxylic acid group and a phenyl ring. Fifteen capping groups were synthesized and ligated with the tetra peptide RLIF (SEQ ID NO: 35). The synthetic schemes for pyrazoles, furan and pyrroles are outlined in scheme 1a, 1b and 1c respectively.

Scheme 1a:

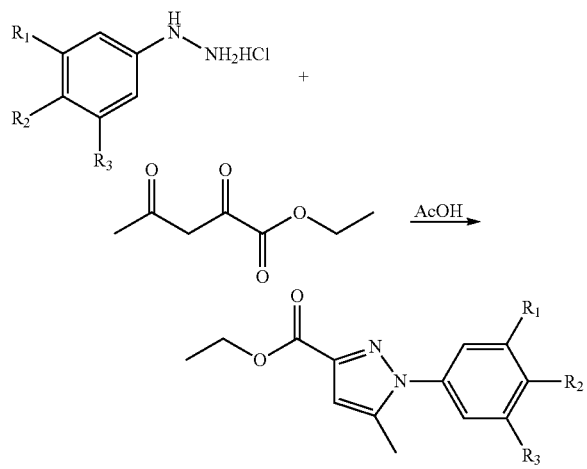

Scheme 1b:

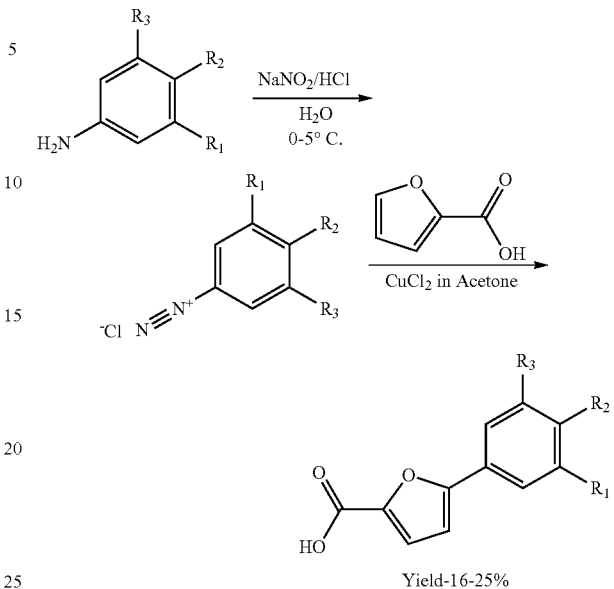

Scheme 1c:

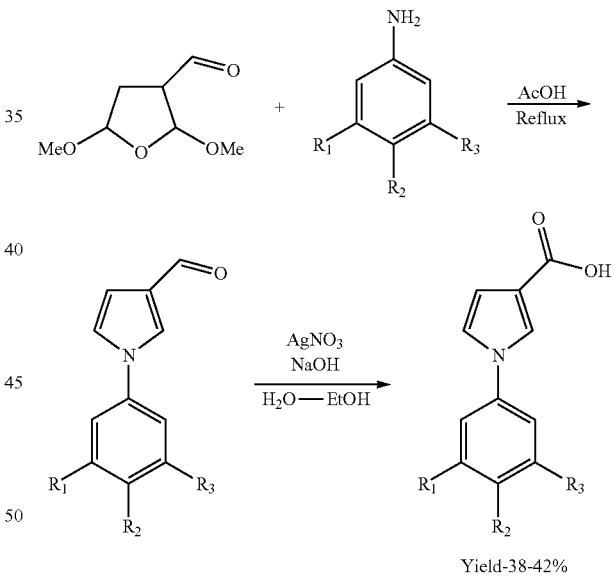

The X-ray crystal structure of (1-(3,5-dichlorophenyl)-5-methyl-1H-1,2,4-triazole-3-carbonyl-RLIF (SEQ ID NO: 36) shows that the N-cap hydrogen bonds with Trp217 and Gln 254 of cyclin A. SAR information in Table 6, below reveals the following:

Triazole N-caps were found to be the most potent of the tested compounds, followed by pyrazole and furan. The 4-chloro substitutions on the phenyl ring are the most effective, followed by 3,5-dichloro substituted compounds.

Pyrrole and thiazole show significantly lower activity than the triazole Ncaps.

TABLE 6

| SCCP ID | R1 | R2 | R3 | R4 | W | X | Y | Z | CDK2/cyclin A IC$_{50}$ (μM) | CDK4/cyclin D1 IC$_{50}$ (μM) |
|---|---|---|---|---|---|---|---|---|---|---|
| 5773 | Triazole | Cl | H | Cl | CH3 | N | N | N | C | ~20 | 30 |
| 5774 | | H | Cl | H | CH3 | N | N | N | C | ~100 | 13 |
| 5762 | Pyrazole | H | H | H | CH$_3$ | N | N | C | C | | ~50 |
| 5764 | | Cl | H | H | CH$_3$ | N | N | C | C | | ~100 |
| 5771 | | F | H | H | CH$_3$ | N | N | C | C | | ~100 |
| 5765 | | H | Cl | H | CH$_3$ | N | N | C | C | | 39 |
| 5766 | | OCH$_3$ | H | H | CH$_3$ | N | N | C | C | ~100 | 120 |
| 5776 | Pyrrole | H | Cl | H | H | N | C | C | C | | >180 |
| 5775 | | Cl | H | Cl | H | N | C | C | C | | >180 |
| 5768 | Furan | Cl | H | Cl | H | C | O | C | C | | ~200 |
| 5772 | | F | H | H | H | C | O | C | C | | >180 |
| 5770 | | H | Cl | H | H | C | O | C | C | | 200 |
| 5588 | | OCH$_3$ | H | H | H | C | O | C | C | | >180 |
| 5587 | | CH$_3$ | H | H | H | C | O | C | C | | 80 |
| 5583 | Thiazole | H | Cl | H | H | C | N | C | S | | >180 |

Structures for each of the capping groups of Table 6 are as follows:

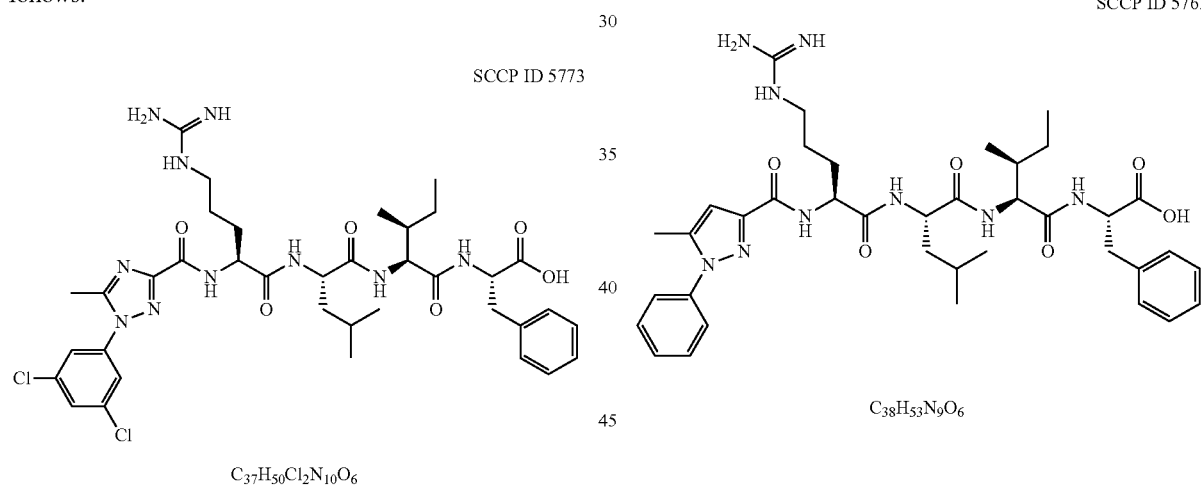

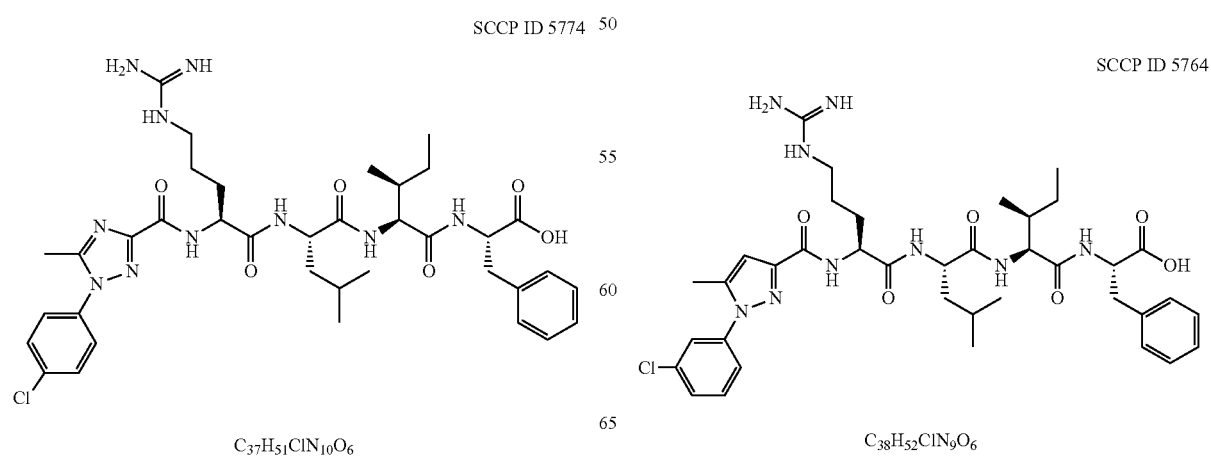

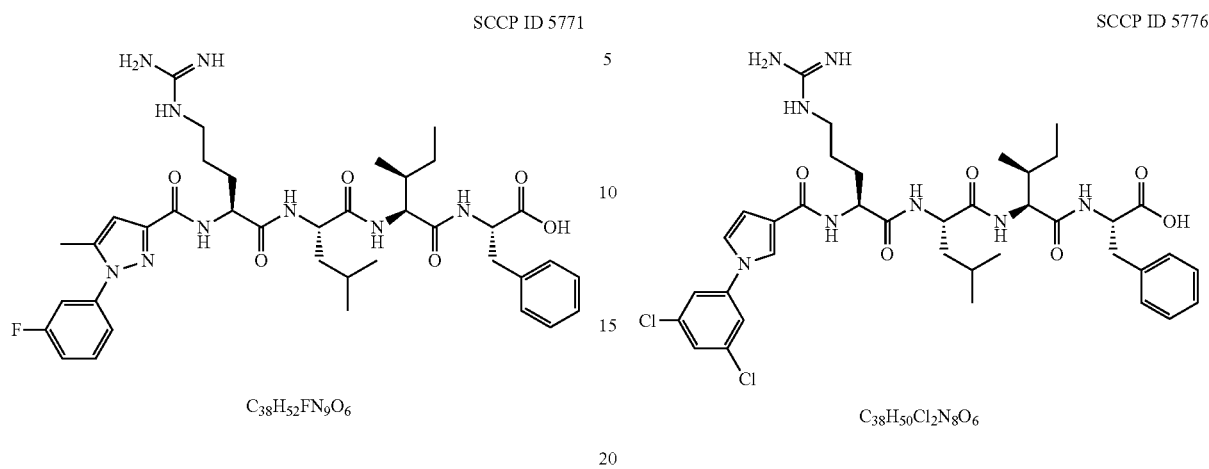
SCCP ID 5771
C$_{38}$H$_{52}$FN$_9$O$_6$
SCCP ID 5776
C$_{38}$H$_{50}$Cl$_2$N$_8$O$_6$
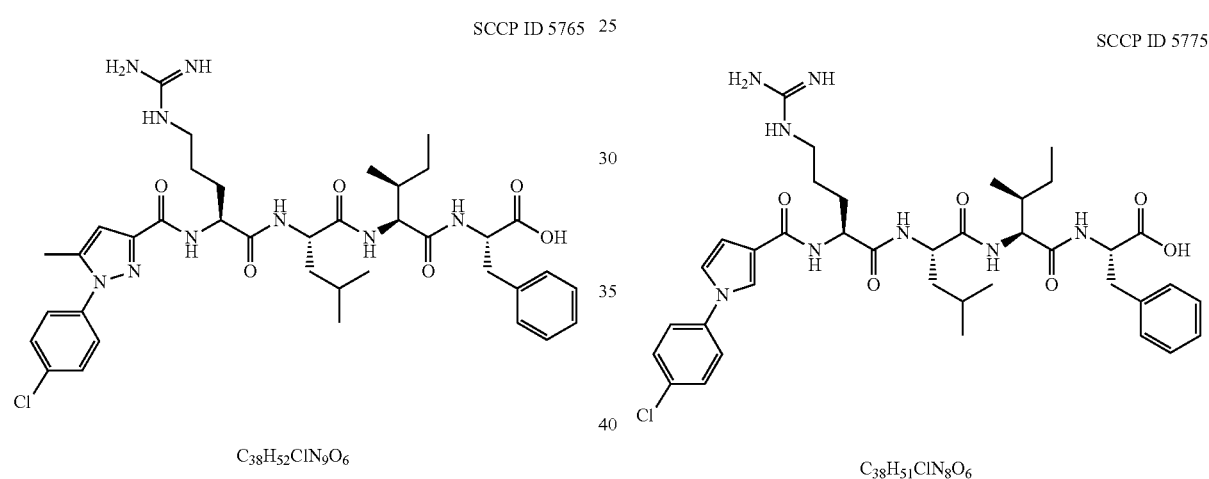
SCCP ID 5765
C$_{38}$H$_{52}$ClN$_9$O$_6$
SCCP ID 5775
C$_{38}$H$_{51}$ClN$_8$O$_6$
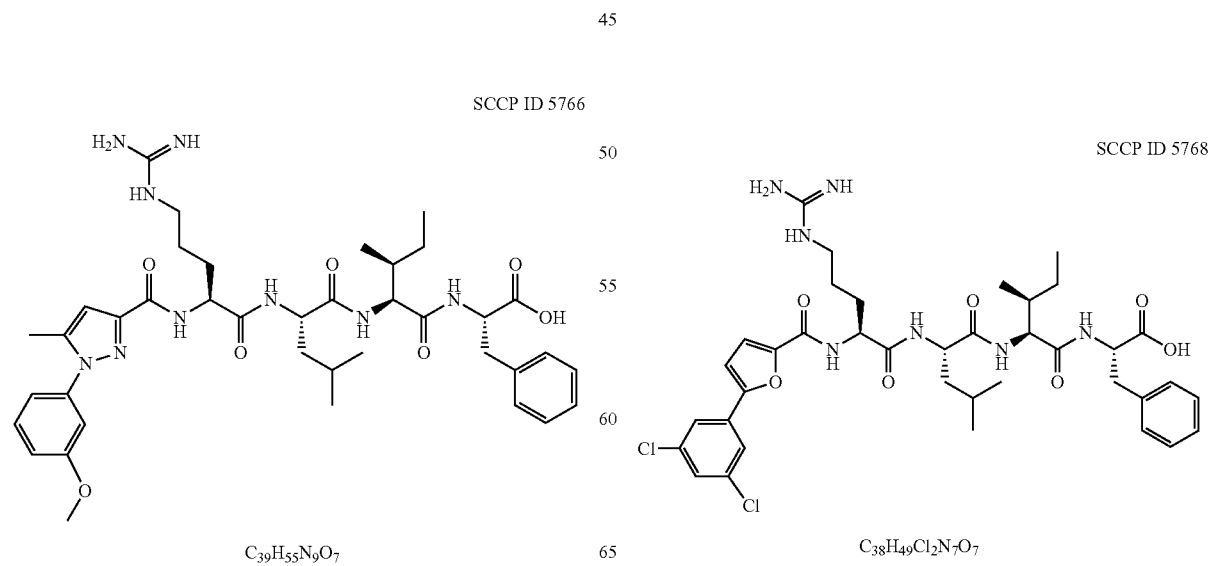
SCCP ID 5766
C$_{39}$H$_{55}$N$_9$O$_7$
SCCP ID 5768
C$_{38}$H$_{49}$Cl$_2$N$_7$O$_7$

23

-continued

SCCP ID 5772

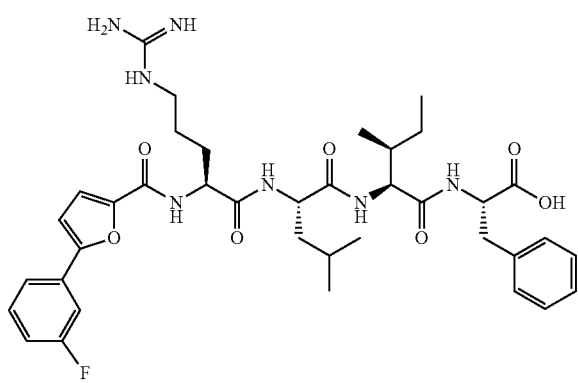

C38H50FN7O7

SCCP ID 5770

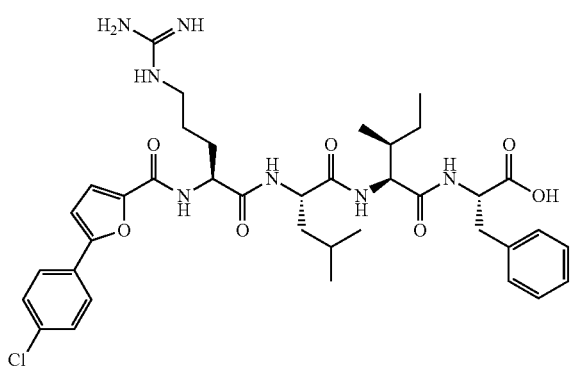

C38H50ClN7O7

SCCP ID 5588

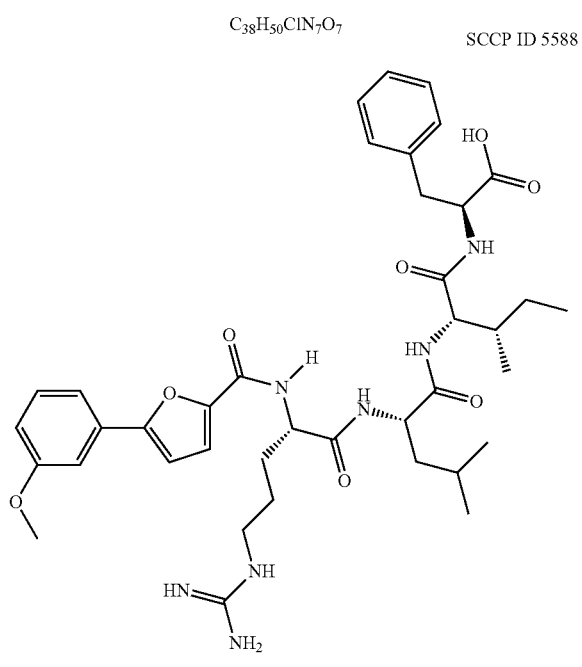

C39H53N7O8

24

-continued

SCCP ID 5587

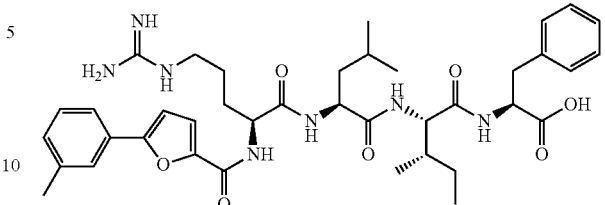

C39H53N7O7

SCCP ID 5583

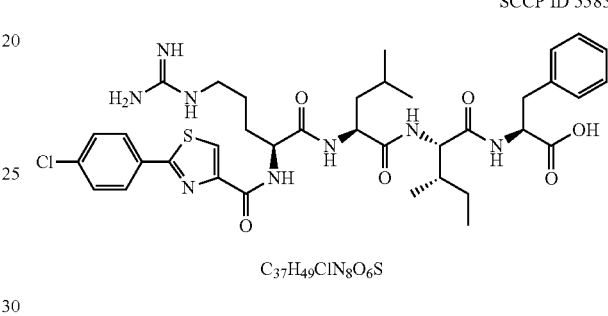

C37H49ClN8O6S

The validation was carried out to ensure that the method was efficient to produce reproducible results and to show that the docking results of the unknown compounds were predictive. Two native ligands (1-(3,5-dichlorophenyl)-5-methyl-1H-1,2,4-triazole-3-carbonyl and 1-(4-chlorophenyl)-5-methyl-1H-1,2,4-triazole-3-carbonyl) and a negative control were docked in both the sub units A and B of CDK2/Cyclin A crystal structure. The variation in the parameters (i) energy grid (Dreiding, OFF and PLP1), (ii) minimization sphere (on or off) and (iii) number of poses generated (20, 10 and 5) was carried out.

For each parameter, the number of correct poses (poses that are superimposible with the crystal structure binding mode) of the positive control ligands generated, the number of negative control poses in top 25 poses, the best scoring functions that gave more number of correct poses in top ranking order were studied. The optimized parameters are energy grid PLP1 with minimization sphere on and number of poses 10 and the scoring function PLP1. The docking of the native ligands were reproducible with the optimized parameters. The results are shown in Table 8.

TABLE 8

| Energy Grid | Dreiding | CFF | PLP1 |
|---|---|---|---|
| No. of correct poses 3,5-DCPT | 2 | 4 | 6 |
| No. of correct poses 4-DCPT | | | 8 |

TABLE 8-continued

| Energy Grid | Dreiding | CFF | PLP1 |
|---|---|---|---|
| Negative controls in top 25 | -PLP1(4), -PLP2(4), Jain (4), PMF(4), DOCK SCORE(6) | -PMF (7), DOCK SCORE (6) | No -ve control poses in all the scoring functions |
| Best scoring function | LigScore2_Dreiding | PLP1, PLP2 | PLP1, PLP2 |
| 3,5-DCPT (rank of top 25 correct/closer poses for the best scoring function | 4,5 (for all the scoring functions) | PLP1(9, 10, 11, 12, 25), PLP2(13, 14, 15, 16, 25) | PLP1(7, 8, 9, 10, 14, 11, 12, 13, 25), PLP2(11, 12, 13, 14, 18, 15, 16, 17) |
| 4-DCPT (rank of top 25 correct/closer poses for the best scoring function) | | PLP1(1, 2, 3, 4, 5, 6, 7, 8), PLP2(17, 18, 19, 20, 21, 22, 23, 24) | PLP1(1, 2, 3, 4, 5, 6) PLP2(20, 21, 22, 23, 24, 25) |

Molecules may be designed on the basis of one or more of: (i) Molecular weight less than 250, (ii) absence of charge on the molecules to improve permeation, (iii) Presence of a carboxylic acid group which is essential for ligation to the peptide and (iv) Commercial availability and synthetic feasibility.

Various N-capping group designs are shown below. The scheme for development of the designs generally includes:
1. Ring A is replaced with 5 membered or six membered heterocycles
2. Ring B was replaced with phenyl group or heterocycles
3. Spacer between two rings
4. Spacers before the carbonyl group.

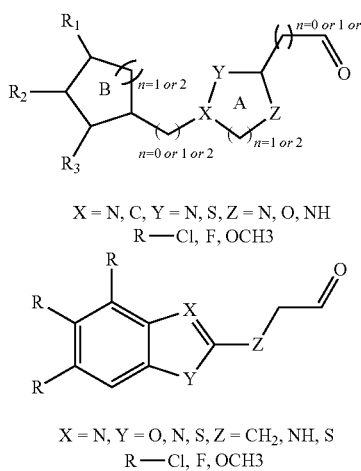

X = N, C, Y = N, S, Z = N, O, NH
R — Cl, F, OCH3

X = N, Y = O, N, S, Z = CH$_2$, NH, S
R — Cl, F, OCH3

Modeling the Interactions of p27 with Cyclin D1 Structures

CDK4/cyclin D1 have been shown to associate with p27 and that this interaction promotes the formation of the complex. It is also known that different states of the ternary complex exist, where p27 may bind to generate inhibited and non-inhibited CDK4 species. A critical aspect of this process is the phosphorylation of p27 on Y88, sited on the 3$_{10}$ helix which inserts into the ATP binding site of CDK4 in the inhibited complex. Phosphorylation presumably leads to dissociation of the helix from the ATP cleft through disruption of hinge H-bonding interactions and through repulsion of the phosphate with nearby acidic residues. In this non-inhibited form, p27 however, must still maintain affinity for the complex in order to sequester the inhibitor from CDK2/cyclin E complexes and allow cell cycle progression. A major contribution to this binding is through cyclin D1/p27 interactions and assisted by the CBM and other residues. So as to construct a model structure of p27/cyclin D1 interactions, cyclin D1 isolated from the 2W96 crystal structure was overlayed with the CDK2/cyclin A/p27 ternary complex (1JSU). After deletion of the CDK2, cyclin A and non cyclin D1 interacting p27 residues, the newly formed complex was subjected to energy minimization. After convergence of the structure to a suitable minimum, and examination of the resulting interactions, a plausible structural basis for the interactions of p27 with cyclin D1 interactions was described. Subsequent to generation of this structure, the interaction energies of individual p27 residues with cyclin D1 were generated and compared with those for cyclin A. Significant differences in the intermolecular interactions are apparent for several residues, several of which are noted in the octapeptide complexes described in the above sections. These include, A28, N31, F33, V36, L41 and L45. Comparison of the molecular surface for the p27 interacting residues of cyclin A vs. those of cyclin D1 indicated that profound differences exist specifically in the region where the C-terminus of the inhibitory protein exits from the primary hydrophobic pocket. The more extensive cleft of cyclin D1, led to the hypothesis that incorporation of a suitable residue C-terminal to the glycine would lead to preferential binding vs. cyclin A. Computational design of a number of different residues suggested that methionine would be a good candidate for more optimal interactions and therefore synthesis and testing of the p27 sequences shown in Table 5, was completed and confirmed this conclusion.

Figure 4:
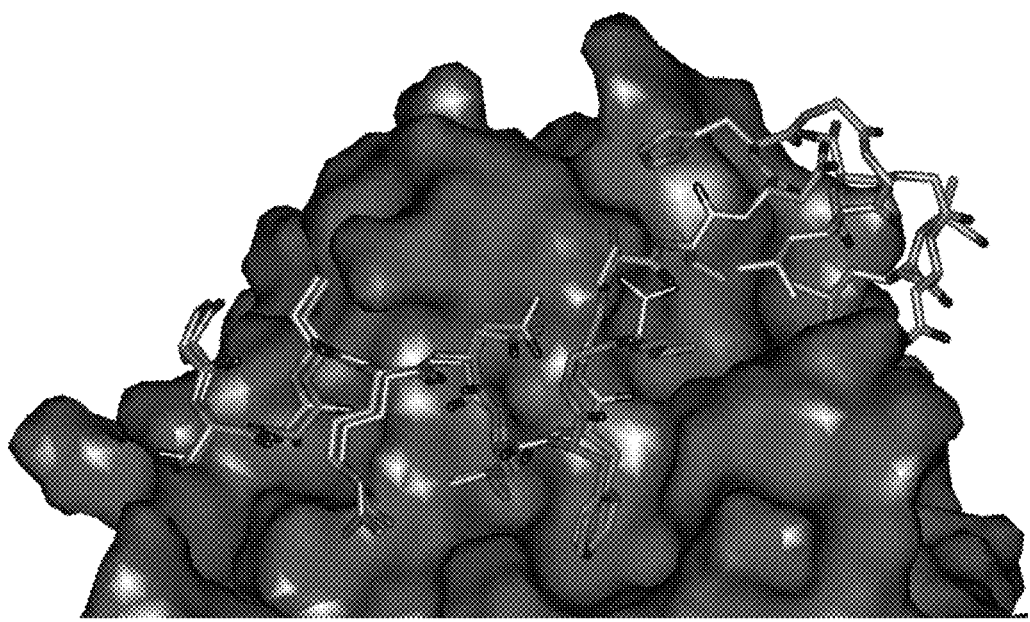
FIG. 4 illustrates a modeled complex of the p27 residues 25-49 with cyclin D1 (2W96) overlaid with SAKRNLFGM (SEQ ID NO: 1).

FIG. 4 illustrates a modeled complex of p27 residues 25-49 with Cyclin D1 (2W96) overlayed with SAKRNLFGM (SEQ ID NO: 1). The P35 and V36 interacting site on cyclin D1 is the region shown to provide a more extensive hydrophobic pocket than in the cyclin A2 context and which was exploited by methionine substitution. As may be seen in FIG. 4, the P35 and V36 contacting site of cyclin D1 has a larger accessible volume and therefore has suboptimal interactions with p27. This was confirmed in the per residue interaction energy calculation which yielded values of −1.9 and −3.6 kcal/mol for D1 and A respectively. The lack of increase of the Asparagine containing sequence may be explained by the formation of an intramolecular H-bond observed in the crystal structure and which precludes optimal interactions of the methionine. Substitution of this residue with an alanine resulted in a 2 fold potency enhancement as predicted. As illustrated (FIG. 4), the linear side chain of the P35M analog extends with a high degree of complementarity into the extension of the primary hydrophobic pocket. These results suggest that this extended binding site in cyclin D1 could be exploited in the design of small molecule cyclin groove inhibitors.

In summation, comparison of the cyclin binding grooves of cyclin D1 structures obtained recently through crystallographic studies provides considerable insight into the structural requirements for cyclin A2 vs. D1 selectivity and for differential binding of CGI peptide analogues. While the binding of peptide inhibitors of cyclin A and E substrate recruitment has been extensively characterized, little information has been made available describing the determinants of cyclin D inhibition. Structural analysis revealed that two key amino acid substitutions in the cyclin D1 groove have a major impact on peptide inhibitor binding. Exchange of one of the two acidic residues interacting with Arg4 (Asp216 and Glu220), with Thr62 significantly decreases the calculated enthalpic contribution to binding and is suggestive of a large decrease in affinity. In order to determine if the predicted decrease in the electrostatic interaction energy is significant in contributing to cyclin A selectivity, the arginine isostere citrullene was incorporated into the p21 8mer, HAKCitRLIF (SEQ ID NO: 26) (Table 5). It was predicted that due to the less acidic environment of the Arg contacting residues in cyclin D, that the potency decrease would be less marked in this context. In reality however, a similar drop off was demonstrated in both scenarios and thus indicating otherwise. Closer examination of the peptide-cyclin D1 structure suggests that the urea carbonyl of citrullene is within H-bonding distance of the OH group of Thr62. This interaction would therefore compensate for the decreased capacity to ion pair and result in a similar potency decrease.

As described, the second major difference between the two cyclins is in the exchange of Leu214 in cyclin A for Val60 in cyclin D. The smaller Valine sidechain projects down toward the base of this hydrophobic pocket with the net effect that the □ methyls are brought into closer proximity to the peptide inhibitor side chains which insert into this pocket. This substitution therefore decreases the volume of the primary hydrophobic pocket in the latter and thereby results in lower affinity of CGI peptides containing phenylalanine. Cyclin bound complexes were generated for a series of peptides previously determined to have varying affinities for cyclin A and cyclin D1 and possessing different C-terminal sequences. The calculated binding energies for these complexes correlated well not only for IC50s determined for cyclin A and D1 individually but also for the selectivity of the peptides observed. These results therefore determined that in addition to the X-ray structures used, the model structures for the peptide-cyclin complexes gave valid results and that this information is useful in the potential design and optimization of improved cyclin D1 inhibitors. From these observations, the hypothesis was proposed that due to the decreased volume of the primary hydrophobic pocket relative to cyclin A, that the incorporation of non-natural amino acids with differing cyclic sidechains than phenylalanine might be tolerated to a greater degree. To this end, the results presented confirm that this is indeed the case however these are dependent on the peptide context. As has been previously structurally characterized, the presence of a spacer residue between the critical Leu and Phe functions to allow a geometrical arrangement of the two side chains that interacts with a greater degree of complementarity and therefore increases binding affinity relative to peptides with no spacer. The results suggest that non-spacer containing peptide, SAKRRLXG (SEQ ID NO: 2), has a binding mode which is more conducive and tolerant of smaller cyclic sidechains. In order to probe this further, a 3D structure for each of the synthesized analogs in complex with both cyclins was generated and further to this, their non-bonded interaction energy calculated. These results suggested that a correlation between the observed potencies and the calculated affinity existed and confirmed that for both 5 membered rings, a decrease in binding of these analogues would be expected. The structural basis for the greater affinity of the furylalanine (X1) vs. the 2-thienylalanine (X2) in the p107 context is apparent from the modeled structure. The closer proximity of the heteroatom to Val60 in the peptide without the spacer residue results in displacement of the larger sulfur containing Phe replacement (thiophene ring) and lower relative affinity. In the p21 peptide, the conformational preference allowed by the spacer residue, results in the heteroatom pointing to the back wall of the primary hydrophobic pocket, away from Val60. As the heteroatom projects into more expansive region, the larger sulfur atom provides greater complementarity with K96 and Q100 resulting in increased affinity in the thienylalanine derivative. Changing the context of the heterocyclic sulfur atom as in X3 resulted in potency increase of SAKRRLX3G (SEQ ID NO: 11) for cyclin A but an increase in cyclin D1 affinity. The larger hydrophobic pocket in cyclin A may accommodate the bulky sulfur atom more readily than may the cyclin D1 site decreased in volume by Val60, Examination of the intermolecular contacts for the cyclohexylalanine derivative X6, a bulkier Phe replacement as a result of the unsaturated ring, again provided insight into the differing potencies for peptides containing this residue with cyclin D1. Modeling of the complex of SAKRRLX6G (SEQ ID NO: 14) with cyclin D1 (12 fold decrease in IC50), suggested that in order to maintain productive binding, the CHA sidechain is brought in close proximity to Val60 resulting in unfavorable contacts. For the HAKRRLIX6 (SEQ ID NO: 22) inhibitor (4 fold loss in potency), the sidechain may adopt a more favorable position, contacting several residues of the primary binding site in line with its higher relative potency. The dramatic decreases in inhibition of the pyridylalanine derivatives X7 and X8 relative to the native phenylalanine cannot readily explained in terms of different interactions with the cyclin groove. A probable scenario is that the pyridyl ring is solvated to a greater degree relative to the phenyl and therefore a desolvation penalty would disfavor binding. A number of substitutions in the cyclin groove recognition motif have been incorporated in the N-terminal and arginine binding site and provide additional information on the tolerance of sequence changes upon binding to the secondary hydrophobic and acidic regions of cyclin D1.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A peptide inhibitor having the sequence of SAKRRL(X3)G (SEQ ID NO: 11) in which X3 has the following structure:

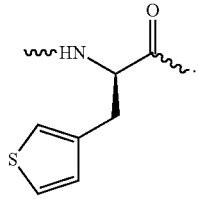

2. A peptide inhibitor having the formula of RL(X3)G in which X3 has the following structure:

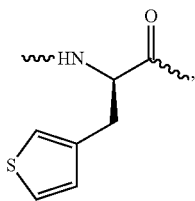

the N-terminus of the said peptide inhibitor comprises an N-terminal N-cap: 1-(3,5-dichlorophenyl)-5-methyl-1H-1,2,4-triazole-3-carboxylic acid wherein the triazole moiety of the N-cap is optionally replaced with an isostere.

3. The peptide inhibitor according to claim 2, the isostere is a pyrazole, furoic acid, pyrrole, or thiazole.

* * * * *